(12) United States Patent
Pomares et al.

(10) Patent No.: US 8,513,438 B2
(45) Date of Patent: Aug. 20, 2013

(54) PROCESS FOR THE PREPARATION OF (6S)-(−)-5,6,7,8-TETRAHYDRO-6-[PROPYL-(2-THIENYL)ETHYL]AMINO-1-NAPHTHOL (ROTIGOTINE)

(75) Inventors: Marta Pomares, Sant Cugat del Vallès (ES); Francisco Marquillas Olondriz, Barcelona (ES)

(73) Assignee: Interquim, S.A., Sant Cugat del Valles (ES)

( * ) Notice: Subject to any disclaimer, the term of this patent is extended or adjusted under 35 U.S.C. 154(b) by 171 days.

(21) Appl. No.: 13/133,898

(22) PCT Filed: Dec. 9, 2009

(86) PCT No.: PCT/EP2009/066662
§ 371 (c)(1),
(2), (4) Date: Aug. 30, 2011

(87) PCT Pub. No.: WO2010/066755
PCT Pub. Date: Jun. 17, 2010

(65) Prior Publication Data
US 2011/0306776 A1 Dec. 15, 2011

(30) Foreign Application Priority Data
Dec. 9, 2008 (ES) .................................. 200803472

(51) Int. Cl.
*C07D 333/20* (2006.01)

(52) U.S. Cl.
USPC ............................................................ 549/74

(58) Field of Classification Search
USPC ............................................................. 549/74
See application file for complete search history.

(56) References Cited

U.S. PATENT DOCUMENTS 5,407,956 A * 4/1995 Santangelo et al. .......... 514/510
6,372,920 B1 * 4/2002 Minaskanian et al. .......... 549/75

* cited by examiner

*Primary Examiner* — Taofiq A Solola
(74) *Attorney, Agent, or Firm* — Birch, Stewart, Kolasch & Birch, LLP

(57) ABSTRACT

The present invention describes a novel process for the preparation of (6S)-(−)-5,6,7,8-tetrahydro-6-[propyl-(2-thienyl)ethyl]amino-1-naphthol (Rotigotine) comprising: (a) acetylating (S)-(−)-5-hydroxy-N-n-propyl-2-aminotetraline to afford the acetate; (b) reacting this acetate, (−)-5-acetoxy-N-n-propyl-2-aminotetraline, with 2-(2-thienyl)ethanol 2-nitrobenzenesulfonate; (d) hydrolyzing (6S)-(−)-1-acetoxy-5,6,7,8-tetrahydro-6-[propyl-(2-thienyl)ethyl]amino-1-naphthalene to afford (6S)-(−)-5,6,7,8-tetrahydro-6-[propyl-(2-thienyl)ethyl]amino-1-naphthol (Rotigotine) and (d) purifying rotigotine either by the acetylation reaction and subsequent hydrolysis of the formed acetate or by salification of rotigotine through hydrochloride or hydrobromide formation and subsequent base release. Rotigotine is a dopamine agonist and is indicated for the treatment of Parkinson's disease.

17 Claims, No Drawings

PROCESS FOR THE PREPARATION OF (6S)-(−)-5,6,7,8-TETRAHYDRO-6-[PROPYL-(2-THIENYL)ETHYL]AMINO-1-NAPHTHOL (ROTIGOTINE)

FIELD OF THE INVENTION

The invention relates to a process for preparing (6S)-(−)-5,6,7,8-tetrahydro-6-[propyl-(2-thienyl)ethyl]amino-1-naphthol (Rotigotine) (I).

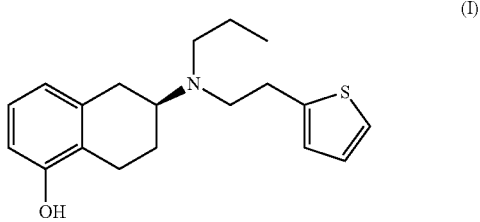 [SMILES: CCCN(CCc1cccs1)[C@H]1CCc2c(O)cccc2C1]

(I)

BACKGROUND OF THE INVENTION

U.S. Pat. No. 4,654,628 describes alkyl aminotetraline derivatives exhibiting dopaminergic activity. Among these compounds, rac-(I) is found,

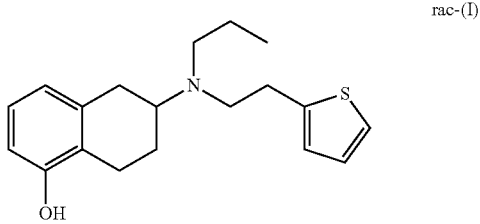 [SMILES: CCCN(CCc1cccs1)C1CCc2c(O)cccc2C1]

rac-(I)

Subsequent studies, whose results are described in U.S. Pat. No. 4,657,925, show that the dopaminergic action of enantiomer (6S)-(−)-5,6,7,8-tetrahydro-6-[propyl-(2-thienyl)ethyl]amino-1-naphthol, hereinafter referred to as (I), is up to 140 times higher than that of its enantiomer (6R)-(+)-5,6,7,8-tetrahydro-6-[propyl-(2-thienyl)ethyl]amino-1-naphthol.

U.S. Pat. No. 4,885,308 describes the use of (I), active ingredient known as Rotigotine, for the treatment of Parkinson's disease.

There is, therefore, a need for a process to prepare this active ingredient.

In the processes described so far—U.S. Pat. No. 4,654,628 and U.S. Pat. No. 4,657,925—for the preparation of rac-(I), the last synthesis step relies on the deprotection of a phenol group by hydrolysis of the corresponding methyl ether. This hydrolysis requires drastic acid conditions, e.g., 48% HBr at high temperature (*J. Med. Chem.*, 1979, v. 22, n. 12, 1469-1475) or BBr$_3$ at low temperature (*Pharmaceutisch Weekblad Scientific Edition*, 1985, 7, 208-211). Due to the fact that the thienyl group is not very stable against these acid conditions, a large number of impurities are formed in this final synthesis step.

U.S. Pat. No. 6,372,920B1 discloses the preparation of (I) by alkylation of (−)-5-hydroxy-N-n-propyl-2-aminotetraline (V) with a large excess of 2-(2-thienyl)ethanol 4-toluenesulfonate in xylene at reflux for 32 hours in the presence of sodium carbonate at 0.6 molar ratio in relation to the starting aminotetraline. According to the authors, the use of alkali metal carbonates or bicarbonates with a molar ratio value lower than 1.9 in relation to the starting aminotetraline reduces the formation of byproducts. However, according to our own experience, in the O-alkylation of phenol, a considerable number of compounds are formed as byproducts.

In accordance with the above, none of the preparation methods for (I) described so far seems to be satisfactory for its industrial application. There is, therefore, a need to provide an alternative industrial process for the preparation of rotigotine (I).

SUMMARY OF THE INVENTION

The invention confronts with the problem of providing an alternative process susceptible of being applied at industrial level for the preparation of compound (6S)-(+)-5,6,7,8-tetrahydro-6-[propyl-(2-thienyl)ethyl]amino-1-naphthol (I) with a high purity that affords its use as a medicament.

The solution provided in this invention is based on the fact that the inventors have observed that by alkylating previously protected (S)-(−)-5-hydroxy-N-n-propyl-2-aminotetraline (V), in the form of a linear or branched alkyl ester or phenylalkyl (III), with a compound of general formula (IV) wherein L is a leaving group selected from the group consisting of halogens, preferably chloro and bromo, and sulfonates, preferably methanesulfonate, 2-nitrobenzenesulfonate, 3-nitrobenzenesulfonate, 4-nitrobenzenesulfonate and 4-toluenesulfonate, the secondary O-alkylation reaction of phenol is avoided, thus obtaining (6S)-(−)-1-acyloxy-5,6,7,8-tetrahydro-6-[propyl-(2-thienyl)ethyl]amino-1-naphthalene (II).

Moreover, the inventors propose the specific use of nitrobenzenesulfonates as alkylating agents which, on being more reactive than methanesulfonate or 4-toluenesulfonate, facilitate the use of milder reaction conditions.

Subsequently, hydrolysis of the ester group of (II) under mild conditions afforded highly pure (6S)-(−)-5,6,7,8-tetrahydro-6-[propyl-(2-thienyl)ethyl]amino-1-naphthol, (I).

Likewise, another solution provided by this invention is based on the fact that the inventors have observed that a purification method for (6S)-(−)-5,6,7,8-tetrahydro-6-[propyl-(2-thienyl)ethyl]amino-1-naphthol (I) consisting in acylating the phenol with an acylating agent, which is selected between the corresponding acyl chloride of formula RCOCl and the corresponding acid anhydride of formula (RCO)$_2$O, allows to obtain (6S)-(−)-1-acyloxy-5,6,7,8-tetrahydro-6-[propyl-(2-thienyl)ethyl]amino-1-naphthalene (II,) with higher purity. Then, hydrolysis of this ester under mild conditions yields highly pure (6S)-(−)-5,6,7,8-tetrahydro-6-[propyl-(2-thienyl)ethyl]amino-1-naphthol (I).

In a similar manner, another purification method proposed by the inventors involves salification of final compound (I) with a mineral acid selected between hydrochloric acid and hydrobromic acid, followed by subsequent optional separation of the thus formed salt and its optional crystallization, and final recovery of (I) by treatment of the salt with an inorganic salt selected from the group consisting of alkaline or earth-alkaline carbonates and bicarbonates.

DETAILED DESCRIPTION OF THE INVENTION

The synthetic pathway on which the process for preparing (I) is based, i.e., the object of the present invention, is shown in Scheme 1:

Scheme 1

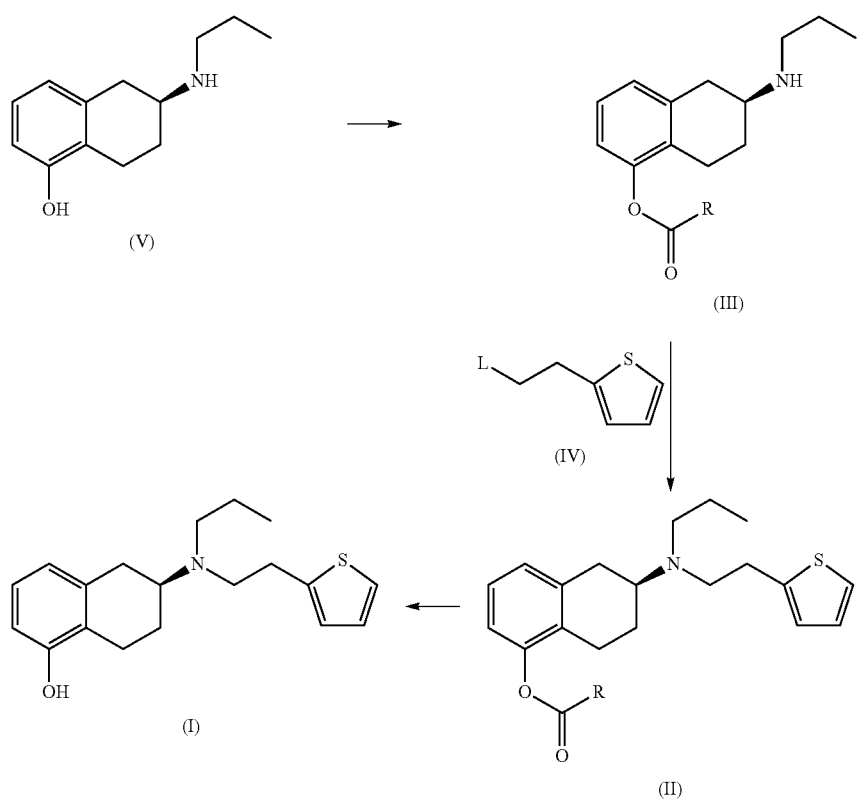

R is selected from the group consisting of linear or branched ($C_1$-$C_4$)-alkyl and ($C_1$-$C_3$)-phenylalkyl.

L is a leaving group selected from the group consisting of halogens, preferably chloro and bromo, and sulfonates, preferably methanesulfonate, 2-nitrobenzenesulfonate, 3-nitrobenzenesulfonate, 4-nitrobenzenesulfonate and 4-toluenesulfonate.

The enantiopure compound (V) may be obtained by any of the methods described in the literature (see Hacksell et al., *J. Med. Chem.*, 1979, vol. 22(12), p. 1469-1475; Sonesson, *J. Med. Chem.*, 1995, vol. 38 y U.S. Pat. No. 5,442,117).

The synthetic pathway proposed by the inventors starts from the O-acylation of phenol (V) in the form of its salt (hydrobromide or hydrochloride), either as isolated product or in situ as the reaction medium, with an acylating agent (acid chloride, RCOCl, or acid anhydride, $(RCO)_2O$) to obtain (−)-5-acyloxy-N-n-propyl-2-aminotetraline (III).

In a particular embodiment, the acylating agent is acetyl chloride and the ester formed is (−)-5-acetoxy-N-n-propyl-2-aminotetraline (III').

It is also an object of the present invention the alkylation reaction of the amine (−)-5-acetoxy-N-n-propyl-2-aminotetraline (III') with a compound of general formula (IV) in the presence of a base selected from the group consisting of alkaline and earth-alkaline carbonates and bicarbonates and in an aprotic inert solvent selected from the group consisting of an aliphatic nitrile selected from the group consisting of acetonitrile and propionitrile, and an aliphatic or aromatic hydrocarbon selected from the group consisting of hexane, heptane, octane, 2,5-dimethylhexane, cyclohexane, methylcyclohexane, toluene, o-xylene, m-xylene, p-xylene, ethylbenzene, styrene and cumene, and their mixtures, at the boiling temperature of the mixture, to afford (6S)-(−)-1-acetoxy-5,6,7,8-tetrahydro-6-[propyl-(2-thienyl)ethyl]amino-1-naphthalene, (II').

In a particular embodiment, the leaving group (L) of the compound of general formula (IV) is selected from 2-nitrobenzenesulfonate, 3-nitrobenzenesulfonate and 4-nitrobenzenesulfonate, the solvent is toluene and the base is sodium bicarbonate.

The preparation of 2-(2-thienyl)ethanol nitrobenzenesulfonates is performed by any of the methods described in the literature for the preparation of the analog 2-(2-thienyl)ethanol 4-toluenesulfonate as disclosed in U.S. Pat. No. 4,127,580.

Subsequently, (II) is hydrolyzed in the presence of a coadjuvant selected from:

a1) an alkaline or earth-alkaline hydroxide selected from the group consisting of sodium hydroxide, potassium hydroxide and calcium hydroxide, preferably sodium hydroxide and potassium hydroxide; or a2) an aqueous solution containing a mineral acid selected from the group consisting of hydrochloric acid, hydrobromic acid, sulfuric acid and phosphoric acid, preferably hydrochloric acid;

in a medium constituted by water, an aliphatic alcohol having at most 4 carbon atoms selected from the group consisting of methanol, ethanol, propanol and isopropanol, and their mixtures, preferably water, methanol and ethanol, and their mixtures.

It is also an object of the present invention the purification methods of (6S)-(−)-5,6,7,8-tetrahydro-6-[propyl-(2-thienyl)ethyl]amino-1-naphthol (I) selected among:

a) acylation of (6S)-(−)-5,6,7,8-tetrahydro-6-[propyl-(2-thienyl)ethyl]amino-1-naphthol (I), isolation of the ester (II) and final hydrolysis. In a particular embodiment, the acylating agent is acetyl chloride and (6S)-(−)-1-acetoxy-5,6,7,8-tetrahydro-6-[propyl-(2-thienyl)ethyl]amino-1-naphthalene hydrochloride (II'.HCl) is obtained, which is subsequently hydrolyzed to afford (I) with a higher purity; and b) salification of final compound (I), isolation of the formed salt which can be recrystallized, and subsequent release of the salt by treatment with an inorganic base. In a particular embodiment, the formed salt is a hydrochloride and the subsequent release of the base is performed with potassium carbonate in a water/ethyl acetate biphasic mixture.

EMBODIMENTS OF THE INVENTION

The following examples are additionally given to illustrate the present invention and are not intended to limit the scope of the invention.

Example 1

Preparation of (−)-5-acetoxy-N-n-propyl-2-aminotetraline (III') from (−)-5-hydroxy-N-n-propyl-2-aminotetraline (V)

9.6 g of (−)-5-hydroxy-N-n-propyl-2-aminotetraline (V) were dissolved in 80 mL of acetic acid. Then, the mixture was heated at 35/40° C., 9.8 mL of 33% HBr were added in acetic acid (1.2 equivalents), and kept at this temperature for 30 minutes. Then, the mixture was heated at 45/50° C., 4.5 mL of acetyl chloride (1.35 equivalents) were added, and kept at this temperature for 6 hours. Afterwards, 30 mL of toluene were added and the mixture was slowly cooled at 15/18° C. This temperature was maintained for 2 hours. The suspension was filtered off and the solid obtained was stove dried. 13.8 g of (−)-5-acetoxy-N-n-propyl-2-aminotetraline hydrobromide (III').HBr were obtained (90% yield).

Melting point (DSC peak): 282.48° C.

IR (cm$^{-1}$, KBr): 3434, 2942, 2814, 2787, 1757, 1459, 1451, 1221, 1035

$^1$H-NMR (dmso-d$_6$) δ: 0.91 (t, 3H, NH—CH$_2$—CH$_2$—CH$_3$), 1.61 (m, 3H, NH—CH$_2$—CH$_2$—CH$_3$ y NH—CH—CH$_2$—CH$_2$—C), 2.22 (m, 1H, NH—CH—CH$_2$—CH$_2$—C), 2.25 (s, 1H, OCH$_3$), 2.40-2.52 (m, 1H), 2.69-2.75 (dq, 1H), 2.79-2.86 (dd, 1H), 2.95 (t, 2H, NH—CH$_2$—CH$_2$—CH$_3$), 3.21 (dd, 1H), 3.54 (m, 1H), 6.90 (d, 1H, Ar—H), 7.03 (d, 1H, Ar—H), 7.18 (t, 1H, Ar—H)

In order to release the base and obtain (−)-5-acetoxy-N-n-propyl-2-aminotetraline (III'), 13.6 g of (−)-5-acetoxy-N-n-propyl-2-aminotetraline hydrobromide (III').HBr under stirring were suspended into a mixture of 70 mL of toluene and 140 mL of 10% K$_2$CO$_3$. The biphasic mixture was heated for 30 minutes at 35° C. The layers were separated and washed with water (30 ml). The organic layer was concentrated until removal of the solvent. 10 g (98% yield) of (−)-5-acetoxy-N-n-propyl-2-aminotetraline (III') were obtained as an oil.

IR (cm$^{-1}$, NaCl): 3319, 3067, 3026, 2931, 1763, 1581, 1459, 1369, 1202, 1024

$^1$H-NMR (CDCl$_3$) δ: 0.89 (t, 3H, NH—CH$_2$—CH$_2$—CH$_3$), 1.19 (s ancho, 1H, NH), 1.51 (m, 3H, NH—CH$_2$—CH$_2$—CH$_3$ y NH—CH—CH$_2$—CH$_2$—C), 2.03 (m, 1H, NH—CH—CH$_2$—CH$_2$—C), 2.27 (s, 3H, OCOCH$_3$), 2.48-2.60 (m, 2H, NH—CH—CH$_2$—CH$_2$—C y NH—CH—CH$_2$—C), 2.64 (t, 2H, NH—CH$_2$—CH$_2$—CH$_3$), 2.74 (dt, 1H, NH—CH—CH$_2$—CH$_2$—C), 2.88 (m, 1H, NH—CH), 3.02 (dd, 1H, NH—CH—CH$_2$—C), 6.81 (d, 1H, Ar—H), 6.95 (d, 1H, Ar—H), 7.10 (t, 1H, Ar—H).

Example 2

Preparation of (6S)-(−)-1-acetoxy-5,6,7,8-tetrahydro-6-[propyl-(2-thienyl)ethyl]amino-1-naphthalene hydrochloride (II').HCl from (−)-5-acetoxy-N-n-propyl-2-aminotetraline (III').

10 g of the (−)-5-acetoxy-N-n-propyl-2-aminotetraline (III') obtained in Example 1 were mixed with 9 g of NaHCO$_3$ (2.2 equivalents) and 16 g de 2-(2-thienyl)ethanol 2-nitrobenzenesulfonate (1.05 equivalents) in 60 mL of toluene. The mixture was heated under reflux for 11 hours. After reflux, the mixture was cooled at 80° C. and 80 mL of 10% K$_2$CO$_3$ were added. The layers were separated, and the organic layer was washed with 40 mL of 5% NaHCO$_3$ and then with 40 mL of water. The organic layer was concentrated by distillation until obtaining an oil. The product was converted into its hydrochloride by redissolution in ethyl acetate and addition of HCl in isopropanol. The solid formed was recovered by filtration and dried. 12.7 g of (6S)-(−)-1-acetoxy-5,6,7,8-tetrahydro-6-[propyl-(2-thienyl)ethyl]amino-1-naphthalene hydrochloride were obtained as a white solid (80% yield).

Melting point (DSC peak): 146.62° C.

IR (cm$^{-1}$, KBr): 3445, 3050, 2968, 2938, 2431, 1764, 1462, 1201

$^1$H-NMR (CDCl$_3$) δ: 1.00 (t, 3H), 1.88-2.06 (m, 3H), 2.28 (s, 3H, OCOCH$_3$), 2.61 (m, 2H), 2.87-3.67 (m, 10H), 6.88 (d, 1H, Ar—H), 6.92 (dd, 2H, Ar—H), 7.00 (dd, 1H, Ar—H), 7.16 (m, 2H, Ar—H), 12.31 (s, 1H, NH)

Example 3

Preparation of (6S)-(−)-5,6,7,8-tetrahydro-6-[propyl-(2-thienyl)ethyl]amino-1-naphthol (I) from (6S)-(−)-1-acetoxy-5,6,7,8-tetrahydro-6-[propyl-(2-thienyl)ethyl]amino-1-naphthalene hydrochloride (III').HCl 6 g of the (6S)-(−)-1-acetoxy-5,6,7,8-tetrahydro-6-[propyl-(2-thienyl)ethyl]amino-1-naphthalene hydrochloride (II').HCl obtained in Example 2 were dissolved in 30 mL of methanol and 30 mL of water. Then, a solution of 10M NaOH was added at room temperature until pH=13. The mixture was kept under stirring for 3 hours, then distilled in methanol and neutralized until pH=7.5 with 6M HCl. The product was extracted with 24 mL of ethyl acetate. The organic layer was washed with 12 mL of water and then concentrated by distillation of the solvent. 4 g de (6S)-(−)-5,6,7,8-tetrahydro-6-[propyl-(2-thienyl)ethyl]amino-1-naphthol were obtained as a white solid (85% yield).

Melting point (DSC peak): 78.94° C.

IR (cm$^{-1}$, KBr): 3500, 3098, 3065, 2969, 2932, 1585, 1465, 1281, 775, 701

$^1$H NMR (CDCl$_3$) δ: 0.89 (t, 3H, N—CH$_2$—CH$_2$—CH$_3$); 1.51 (sextuplete, 2H, N—CH$_2$—CH$_2$—CH$_3$); 1.58 (ddd, 1H, N—CH—CH$_2$—CH$_2$—C); 2.10 (ddd, 1H, N—CH—CH$_2$—CH$_2$—C); 2.55 (t, 2H, N—CH$_2$—CH$_2$—CH$_3$); 2.47-2.60 (m, 1H, C—CH$_2$—CHN); 2.67-2.87 (m, 4H, N—CH—CH$_2$—CH$_2$—C y N—CH$_2$—CH$_2$-tiofeno); 2.90 (m, 1H, C—CH$_2$—CHN); 2.92-3.01 (m, 3H, C—CH$_2$—CHN y N—CH$_2$—CH$_2$-tiofeno); 4.83 (s, 1H, OH); 6.57 (d, 1H, Ar—H); 6.67 (d, 1H, Ar—H); 6.80 (d, 1H, Ar—H); 6.90 (dd, 1H, Ar—H); 6.97 (t, 1H, Ar—H); 7.10 (d, 1H, Ar—H)

Example 4

Purification Methods of Rotigotine
a) Acetate Formation and Subsequent Hydrolysis:

Preparation of (6S)-(−)-1-acetoxy-5,6,7,8-tetrahydro-6-[propyl-(2-thienyl)ethyl]amino-1-naphthalene hydrochloride (II').HCl from (6S)-(−)-5,6,7,8-tetrahydro-6-[propyl-(2-thienyl)ethyl]amino-1-naphthol (I)

5 g of the (6S)-(−)-5,6,7,8-tetrahydro-6-[propyl-(2-thienyl)ethyl]amino-1-naphthol (99.53% purity by HPLC) obtained in Example 2 were dissolved in 50 mL of acetic acid under room temperature. Then, the mixture was heated at 45-50° C. and 1.56 ml (1.4 equivalents) of acetyl chloride were added. The mixture was kept at this temperature and under stirring for 7 hours, after which 50 mL of toluene were added. The mixture was concentrated under vacuum until an oil was formed. (6S)-(−)-1-acetoxy-5,6,7,8-tetrahydro-6-[propyl-(2-thienyl)ethyl]amino-1-naphthalene hydrochloride precipitated by addition of 25 mL of ethyl acetate. The mixture was filtered off and the solid was dried. The resulting solid weighed 4.3 g (87% yield) and HPLC purity was 99.75%.

Preparation of (6S)-(−)-5,6,7,8-tetrahydro-6-[propyl-(2-thienyl)ethyl]amino-1-naphthol (I) from (6S)-(−)-1-acetoxy-5,6,7,8-tetrahydro-6-[propyl-(2-thienyl)ethyl]amino-1-naphthalene hydrochloride (II').HCl In the same manner as in Example 3, 4 g of (6S)-(−)-1-acetoxy-5,6,7,8-tetrahydro-6-[propyl-(2-thienyl)ethyl]amino-1-naphthalene hydrochloride were hydrolyzed to afford 2.88 g of (6S)-(−)-5,6,7,8-tetrahydro-6-[propyl-(2-thienyl)ethyl]amino-1-naphthol (90% yield) as a white solid with a HPLC purity of 99.87%.

b) Salification and Subsequent Base Release

Preparation of (6S)-(−)-5,6,7,8-tetrahydro-6-[propyl-(2-thienyl)ethyl]amino-1-naphthol hydrochloride (I).HCl from (6S)-(−)-5,6,7,8-tetrahydro-6-[propyl-(2-thienyl)ethyl]amino-1-naphthol (I)

1 g of the (6S)-(−)-5,6,7,8-tetrahydro-6-[propyl-(2-thienyl)ethyl]amino-1-naphthol (I) obtained in Example 3 (96.58% purity by HPLC) was dissolved in 8 mL of ethyl acetate at room temperature. Then, 1.5 mL of 2.5M HCl solution was added in isopropanol. The mixture was cooled for 3 hours at 0-5° C. and a white solid precipitated. The mixture was filtered off to afford 1 g of (6S)-(−)-5,6,7,8-tetrahydro-6-[propyl-(2-thienyl)ethyl]amino-1-naphthol hydrochloride (90% yield). The product was analyzed by HPLC and its purity was 98.58%.

Melting point (DSC peak): 119.20° C.
IR (cm$^{-1}$, KBr): 3237, 2948, 2631, 1733, 1589, 1466, 1279, 773.

In order to release the base and obtain (6S)-(−)-5,6,7,8-tetrahydro-6-[propyl-(2-thienyl)ethyl]amino-1-naphthol (I), 1 g of (6S)-(−)-5,6,7,8-tetrahydro-6-[propyl-(2-thienyl)ethyl]amino-1-naphthol hydrochloride (I).HCl was suspended in a biphasic mixture of 5 mL of water and 5 mL of ethyl acetate. The mixture was neutralized with potassium carbonate until pH=7.5. The layers were separated, the organic layer was washed with 3 mL of water, and then concentrated by distillation of the solvent to afford 0.8 g of (6S)-(−)-5,6,7,8-tetrahydro-6-[propyl-(2-thienyl)ethyl]amino-1-naphthol as a white solid (90% yield) with 99.0% HPLC purity.

Example 5

Preparation of (6S)-(−)-1-acetoxy-5,6,7,8-tetrahydro-6-[propyl-(2-thienyl)ethyl]amino-1-naphthalene hydrobromide (II').HBr from (−)-5-acetoxy-N-n-propyl-2-aminotetraline, (III').

15 g of the (−)-5-acetoxy-N-n-propyl-2-aminotetraline (III') obtained in Example 1 were mixed with 20.4 g of NaHCO$_3$ (4 equivalents) and 24.8 g of 2-(2-thienyl)ethanol 2-nitrobenzenesulfonate (1.3 equivalents) in 120 mL of isopropyl acetate. The mixture was heated under reflux for 15 hours. After the reflux, the mixture was cooled at 30/35° C. and the salts were filtered off. To the filtrate 30 mL of deionized water were added and pH was adjusted to 12.5 with diluted NaOH. The layers were separated and the organic layer was washed with water. To the organic layer 10 ml of isopropanol and 10.3 g of aqueous 48% HBr were added. The solid formed was recovered by filtration and dried. 23.4 g of (6S)-(−)-1-acetoxy-5,6,7,8-tetrahydro-6-[propyl-(2-thienyl)ethyl]amino-1-naphthalene hydrobromide were obtained as a white solid (87% yield).

$^1$H-NMR (CDCl$_3$) δ: 1.01 (t, 3H), 1.90-2.15 (m, 3H), 2.28 (s, 3H, OCOCH$_3$), 2.64 (m, 2H), 2.88-3.70 (m, 10H), 6.92 (d, 1H, Ar—H), 6.96 (dd, 2H, Ar—H), 7.04 (dd, 1H, Ar—H), 7.20 (m, 2H, Ar—H), 11.57 (s, 1H, NH).

IR (cm$^{-1}$, KBr): 3435, 3052, 2962, 2940, 2611, 1763, 1462, 1201, 1031, 734

Example 6

Preparation of (6S)-(−)-5,6,7,8-tetrahydro-6-[propyl-(2-thienyl)ethyl]amino-1-naphthol (I) from (6S)-(−)-1-acetoxy-5,6,7,8-tetrahydro-6-[propyl-(2-thienyl)ethyl]amino-1-naphthalene hydrobromide (II').HBr 3 g of the (6S)-(−)-1-acetoxy-5,6,7,8-tetrahydro-6-[propyl-(2-thienyl)ethyl]amino-1-naphthalene hydrobromide (II').HBr obtained in Example 5 were dissolved in 24 mL of methanol. Then 1.3 g of 50% NaOH (2.3 eq) solution were added at room temperature. The mixture was kept under stirring for 3 hours. After distilling the methanol, 24 mL of isopropyl acetate were added and the mixture was neutralized with 6M HCl until pH=7.5. The organic layer was washed with 12 mL of water, and concentrated by distillation of solvent. After the addition of methylcyclohexane and n-heptane a white solid precipitated. The solid was dried to afford 1.9 g (87% yield) of a product having the same characteristics as those for the product obtained in Example 3, which was identified as (6S)-(−)-5,6,7,8-tetrahydro-6-[propyl-(2-thienyl)ethyl]amino-1-naphthol (I).

Example 7

Preparation of (6S)-(−)-5,6,7,8-tetrahydro-6-[propyl-(2-thienyl)ethyl]amino-1-naphthol (I) from (6S)-(−)-1-acetoxy-5,6,7,8-tetrahydro-6-[propyl-(2-thienyl)ethyl]amino-1-naphthalene hydrobromide (II').HBr 5.0 g of the (6S)-(−)-1-acetoxy-5,6,7,8-tetrahydro-6-[propyl-(2-thienyl)ethyl]amino-1-naphthalene hydrobromide (II').HBr obtained in Example 2 were dissolved in 15 mL of methanol. Then 2.0 g of 50% NaOH (2.2 equivalents) solution were added. The mixture was kept under stirring for 3 hours at room temperature. Then 5 mL of methanol and 50 mL of deionized water were gradually added. A white precipitate appeared. The reaction mixture was cooled at 0-5° C. for 1 hour. The solid was recovered by filtration and dried. 3.38 g (94% yield) of a product identified as (6S)-(−)-5,6,7,8-tetrahydro-6-[propyl-(2-thienyl)ethyl]amino-1-naphthol (I) were obtained.

The invention claimed is:

1. A process for the preparation of (6S)-(+5,6,7,8-tetrahydro-6-[propyl-(2-thienyl)ethyl]amino-1-naphthol (I):

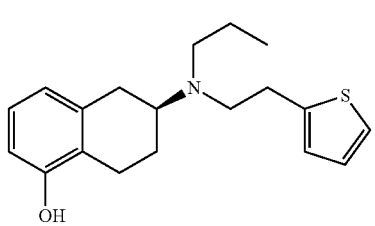

comprising the following steps:
  a) hydrolysis of compound (II):

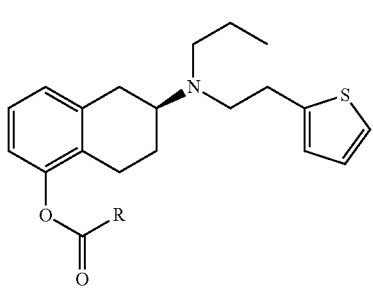

wherein R is a linear or branched ($C_1$-$C_4$)alkyl, in the presence of a coadjuvant selected from the group consisting of:
  a1) an alkaline or earth-alkaline hydroxide selected from the group consisting of sodium hydroxide, potassium hydroxide and calcium hydroxide; and
  a2) an aqueous solution containing a mineral acid selected from the group consisting of hydrochloric acid, hydrobromic acid, sulfuric acid and phosphoric acid;
in a medium comprising water, an aliphatic alcohol having at most 4 carbon atoms selected from the group consisting of methanol, ethanol, propanol and isopropanol, and their mixtures; and
  b) optional purification selected from the group consisting of:
    b1) acylation of final compound (I) with an acylating agent selected from the group consisting of the corresponding acyl chloride of formula RCOCl and the corresponding acid anhydride of formula $(RCO)_2O$, wherein R has the same meaning as above, followed by subsequent separation of the ester (II) thus formed and final hydrolysis according to step a); and
    b2) salification of final compound (I) with a mineral acid selected from the group consisting of hydrochloric acid and hydrobromic acid, followed by subsequent separation of the salt thus formed and its optional crystallization, and final recovery of (I) by treatment of the salt with an inorganic base selected from the group consisting of alkaline or earth-alkaline carbonates and bicarbonates.

2. The process according to claim 1, wherein the preparation of compound (II) comprises alkylation of compound (III):

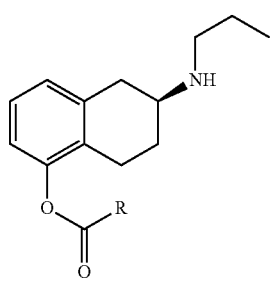

wherein R has the same meaning as above, with a compound of general formula (IV):

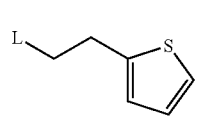

wherein L is a leaving group selected from the group consisting of halogens and sulfonates, in the presence of a base selected from the group consisting of alkaline or earth-alkaline carbonates and bicarbonates, and in an aprotic solvent selected from the group consisting of an aliphatic nitrile selected from the group consisting of acetonitrile and propionitrile, and an aliphatic or aromatic hydrocarbon selected from the group consisting of hexane, heptane, octane, 2,5-dimethylhexane, cyclohexane, methylcyclohexane, toluene, o-xylene, m-xylene, p-xylene, ethylbenzene, styrene and cumene, and their mixtures, at boiling temperature of the mixture.

3. The process according to claim 2, wherein L is selected from the group consisting of 2-nitrobenzenesulfonate, 3-nitrobenzenesulfonate and 4-nitrobenzenesulfonate, the inorganic base is an alkaline bicarbonate, and the solvent is toluene.

4. The process according to claim 2, wherein the preparation of intermediate (III) comprises acylation of compound (V):

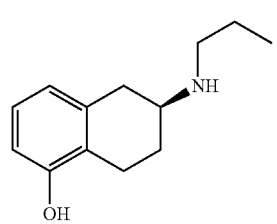

as a salt with a mineral acid selected from the group consisting of hydrobromic acid and hydrochloric acid, with an acylating agent selected from the group consisting of the corresponding acyl chloride of formula RCOCl and the corresponding acid anhydride of formula (RCO)₂O, wherein R has the same meaning as above.

5. The process for the preparation of (6S)-(+5,6,7,8-tetrahydro-6-[propyl-(2-thienyl)ethyl]amino-1-naphthol (I) according to claim 1,

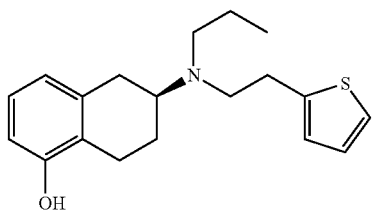
(I)

comprising the following steps:
a) hydrolysis of compound (II'):

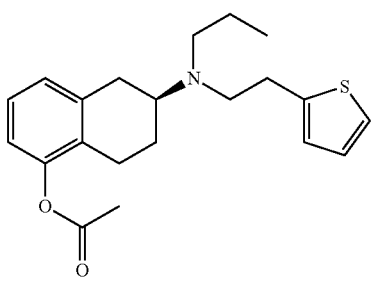
(II')

in the presence of a coadjuvant selected from the group consisting of:
 a1) an alkaline or earth-alkaline hydroxide selected from the group consisting of sodium hydroxide, potassium hydroxide and calcium hydroxide; and
 a2) an aqueous solution containing a mineral acid selected from the group consisting of hydrochloric acid, hydrobromic acid, sulfuric acid and phosphoric acid;
in a medium comprising water, an aliphatic alcohol having at most 4 carbon atoms selected from the group consisting of methanol, ethanol, propanol and isopropanol, and their mixtures;
b) optional purification selected from the group consisting of:
 b1) acetylation of final compound (I) with an acylating agent selected from the group consisting of acetyl chloride and acetic anhydride, followed by subsequent separation of the acetate (II') thus formed and final hydrolysis according to step a); and
 b2) salification of final compound (I) with a mineral acid selected from the group consisting of hydrochloric acid and hydrobromic acid, followed by subsequent optional separation of the salt thus formed and its optional crystallization, and final recovery of (I) by treatment of the salt with an inorganic base selected from the group consisting of alkaline and earth-alkaline carbonates and bicarbonates.

6. The process according to claim 5, wherein the preparation of compound (II') comprises alkylation of compound (III'):

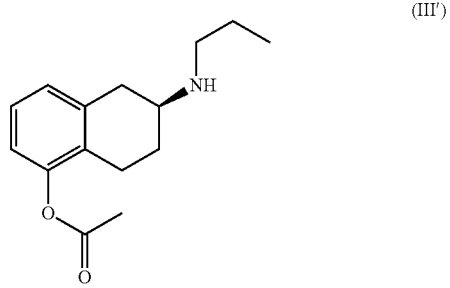 [SMILES: CCCN[C@H]1CCc2c(cccc2OC(C)=O)C1]
(III')

with a compound of general formula (IV):

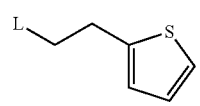
(IV)

wherein L is a leaving group selected from the group consisting of halogens and sulfonates, in the presence of a base selected from the group consisting of alkaline or earth-alkaline carbonates and bicarbonates, and in an aprotic solvent selected from the group consisting of an aliphatic nitrile selected from the group consisting of acetonitrile and propionitrile, and an aliphatic or aromatic hydrocarbon selected from the group consisting of hexane, heptane, octane, 2,5-dimethylhexane, cyclohexane, methylcyclohexane, toluene, o-xylene, m-xylene, p-xylene, ethylbenzene, styrene and cumene, and their mixtures, at boiling temperature of the mixture.

7. The process according to claim 6, wherein L is selected from the group consisting of 2-nitrobenzenesulfonate, 3-nitrobenzenesulfonate and 4-nitrobenzenesulfonate, the inorganic base is an alkaline bicarbonate, and the solvent is toluene.

8. The process according to claim 6, wherein the preparation of intermediate (III') comprises acetylation of compound (V):

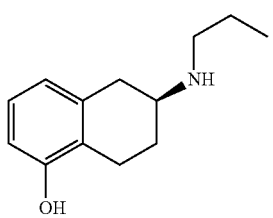
(V)

as a salt with a mineral acid selected from the group consisting of hydrobromic acid and hydrochloric acid, with an acetylating agent selected from the group consisting of acetyl chloride and acetic anhydride.

9. The process for the preparation of (6S)-(+5,6,7,8-tetrahydro-6-[propyl-(2-thienyl)ethyl]amino-1-naphthol (I) according to claim 1,

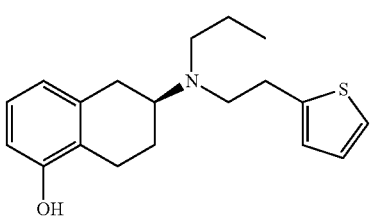

(I)

comprising the following steps:
a) acylation of compound (V):

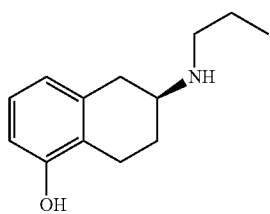

(V)

as a salt with a mineral acid selected from the group consisting of hydrobromic acid and hydrochloric acid, with an acylating agent selected from the group consisting of the corresponding acyl chloride of formula RCOCl and the corresponding acid anhydride of formula (RCO)$_2$O, wherein R is a linear or branched ($C_1$-$C_4$)alkyl,
b) alkylation of the resulting compound (III):

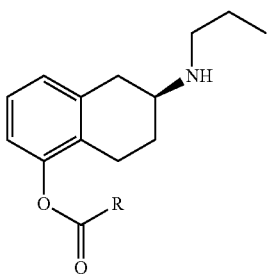

(III)

wherein R has the same meaning as above, with a compound of general formula (IV):

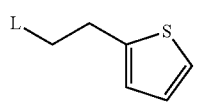

(IV)

wherein L is a leaving group selected from the group consisting of halogens and sulfonates, in the presence of a mineral base selected from the group consisting of alkaline or earth-alkaline carbonates and bicarbonates, and in an aprotic solvent selected from the group consisting of an aliphatic nitrile selected from the group consisting of acetonitrile and propionitrile, and an aliphatic or aromatic hydrocarbon selected from the group consisting of hexane, heptane, octane, 2,5-dimethylhexane, cyclohexane, methylcyclohexane, toluene, o-xylene, m-xylene, p-xylene, ethylbenzene, styrene and cumene, and their mixtures, at boiling temperature of the mixture;
c) hydrolysis of the resulting compound (II):

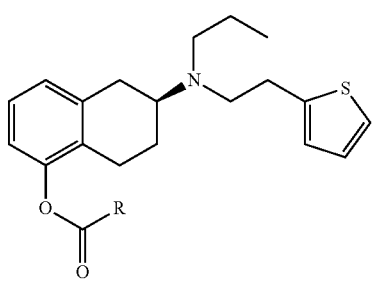

(II)

wherein R has the same meaning as above, in the presence of a coadjuvant selected from the group consisting of:
c1) an alkaline or earth-alkaline hydroxide selected from the group consisting of sodium hydroxide, potassium hydroxide and calcium hydroxide; and
c2) an aqueous solution containing a mineral acid selected from the group consisting of hydrochloric acid, hydrobromic acid, sulfuric acid and phosphoric acid;
in a medium comprising water, an aliphatic alcohol having at most 4 carbon atoms selected from the group consisting of methanol, ethanol, propanol and isopropanol, and their mixtures; and
d) optional purification selected from the group consisting of:
d1) acylation of final compound (I) with an acylating agent selected from the group consisting of the corresponding acyl chloride of formula RCOCl and the corresponding acid anhydride of formula (RCO)$_2$O, wherein R has the same meaning as above, followed by subsequent separation of the ester (II) thus formed and final hydrolysis according to step c); and
d2) salification of final compound (I) with a mineral acid selected from the group consisting of hydrochloric acid and hydrobromic acid, followed by subsequent optional separation of the salt thus formed and its optional crystallization, and final recovery of (I) by treatment of the salt with an inorganic base selected from the group consisting of alkaline and earth-alkaline carbonates and bicarbonates.

10. The process according to step b) of claim 9, wherein L is selected from the group consisting of 2-nitrobenzenesulfonate, 3-nitrobenzenesulfonate and 4-nitrobenzenesulfonate, the inorganic base is an alkaline bicarbonate, preferably sodium bicarbonate, and the solvent is toluene.

11. The process according to claim 1, wherein:
a1) is sodium hydroxide or potassium hydroxide;
a2) is hydrochloric acid;
the medium in step a) comprises water, methanol, ethanol or mixtures thereof; and/or the inorganic base in b2) is selected from the group consisting of sodium carbonate, potassium carbonate, sodium bicarbonate and potassium bicarbonate.

12. The process according to claim 2, wherein:
the halogens are chloro or bromo;
the sulfonates are selected from the group consisting of methanesulfonate, 2-nitrobenzenesulfonate, 3-nitrobenzenesulfonate, 4-nitrobenzenesulfonate and 4-toluenesulfonate; and/or
the base is selected from the group consisting of sodium carbonate, potassium carbonate, sodium bicarbonate and potassium bicarbonate.

13. The process according to claim 3, wherein the inorganic base is sodium bicarbonate.

14. The process according to claim 5, wherein:
a1) is selected from the group consisting of at least one of sodium hydroxide and potassium hydroxide;
a2) is hydrochloric acid;
the medium comprises is at least one member selected from the group consisting of water, methanol and ethanol; and/or
the inorganic base is selected from the group consisting of sodium carbonate, potassium carbonate, sodium bicarbonate and potassium bicarbonate.

15. The process according to claim 6, wherein:
the halogens are chloro or bromo;
the sulfonates are selected from the group consisting of methanesulfonate, 2-nitrobenzenesulfonate, 3-nitrobenzenesulfonate, 4-nitrobenzenesulfonate and 4-toluenesulfonate; and/or
the base is selected from the group consisting of sodium carbonate, potassium carbonate, sodium bicarbonate and potassium bicarbonate.

16. The process according to claim 7, wherein the inorganic base is sodium bicarbonate.

17. The process according to claim 9, wherein:
R is methyl;
the halogens are chloro or bromo;
the sulfonates are selected from the group consisting of methanesulfonate, 2-nitrobenzenesulfonate, 3-nitrobenzenesulfonate, 4-nitrobenzenesulfonate and 4-toluenesulfonate;
the mineral base is selected from the group consisting of sodium carbonate, potassium carbonate, sodium bicarbonate and potassium bicarbonate;
c1) is sodium hydroxide, potassium hydroxide, or mixtures thereof;
c2) is hydrochloric acid; and/or
the medium comprises at least on member selected from the group consisting of water, methanol and ethanol.

* * * * *

UNITED STATES PATENT AND TRADEMARK OFFICE
CERTIFICATE OF CORRECTION

| | | |
|---|---|---|
| PATENT NO. | : 8,513,438 B2 | Page 1 of 1 |
| APPLICATION NO. | : 13/133898 | |
| DATED | : August 20, 2013 | |
| INVENTOR(S) | : Pomares et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 252 days.

Signed and Sealed this
Eighteenth Day of November, 2014

Michelle K. Lee
*Deputy Director of the United States Patent and Trademark Office*